(12) United States Patent
Dos Santos et al.

(10) Patent No.: US 11,006,822 B2
(45) Date of Patent: May 18, 2021

(54) PIXELATED ARRAY OPTICS FOR MIXED MODE SURGICAL LASER ILLUMINATION

(71) Applicant: Novartis AG, Basel (CH)

(72) Inventors: Cesario Dos Santos, Newport Beach, CA (US); Gerald David Bacher, Carlsbad, CA (US); Ronald Smith, Irvine, CA (US); Alireza Mirsepassi, Irvine, CA (US); Michael Papac, North Tustin, CA (US)

(73) Assignee: Alcon Inc., Fribourg (CH)

( * ) Notice: Subject to any disclaimer, the term of this patent is extended or adjusted under 35 U.S.C. 154(b) by 99 days.

(21) Appl. No.: 15/882,867

(22) Filed: Jan. 29, 2018

(65) Prior Publication Data

US 2018/0214018 A1 Aug. 2, 2018

Related U.S. Application Data

(60) Provisional application No. 62/453,728, filed on Feb. 2, 2017.

(51) Int. Cl.
| | |
|---|---|
| *A61B 1/07* | (2006.01) |
| *A61B 3/00* | (2006.01) |
| *A61B 90/30* | (2016.01) |
| *G02B 26/06* | (2006.01) |
| *G02B 23/24* | (2006.01) |
| *G02B 26/08* | (2006.01) |

(52) U.S. Cl.
CPC .............. *A61B 3/0008* (2013.01); *A61B 1/07* (2013.01); *A61B 90/30* (2016.02); *G02B 23/2469* (2013.01); *G02B 26/06* (2013.01); *A61B 2090/306* (2016.02); *G02B 26/0833* (2013.01)

(58) Field of Classification Search
CPC ................ A61B 3/00–185; G02B 23/24–2469
See application file for complete search history.

(56) References Cited

U.S. PATENT DOCUMENTS

| | | | |
|---|---|---|---|
| 5,395,362 A | 3/1995 | Sacharoff et al. | |
| 6,299,307 B1 | 10/2001 | Oltean et al. | |
| 6,464,633 B1 * | 10/2002 | Hosoda | A61B 1/0638 348/68 |
| 7,444,057 B2 | 10/2008 | Dacquay et al. | |
| 7,499,624 B2 | 3/2009 | Dacquay et al. | |
| 7,959,297 B2 | 6/2011 | Silverstein | |
| 8,237,835 B1 * | 8/2012 | Muller | A61B 3/1025 250/201.9 |
| 8,944,647 B2 | 2/2015 | Bueeler | |
| 10,238,543 B2 | 3/2019 | Farley | |
| 10,400,967 B2 * | 9/2019 | Smith | A61B 90/30 |

(Continued)

FOREIGN PATENT DOCUMENTS

| | | |
|---|---|---|
| CN | 103799961 A | 5/2014 |
| EP | 2945005 A1 | 11/2015 |

(Continued)

*Primary Examiner* — Eduardo C Robert
*Assistant Examiner* — Steven J Cotroneo

(57) ABSTRACT

Pixelated array optics for mode mixing may be used to homogenize different modes in an optical fiber used for surgical illumination. A pixelated phase array, such as a digital micromirror device or an LCD phase plate, may impart motion to an incident beam entering the optical fiber to generate a homogeneous illumination field from a coherent light source.

20 Claims, 6 Drawing Sheets

(56) References Cited

U.S. PATENT DOCUMENTS

| | | | |
|---|---|---|---|
| 2003/0025877 A1* | 2/2003 | Yancey | A61B 3/103 351/221 |
| 2003/0076571 A1* | 4/2003 | MacAulay | G02B 23/2453 359/237 |
| 2003/0210378 A1* | 11/2003 | Riza | A61B 3/066 351/205 |
| 2003/0229270 A1 | 12/2003 | Suzuki et al. | |
| 2004/0151008 A1 | 8/2004 | Artsyukhovich et al. | |
| 2005/0027288 A1 | 2/2005 | Oyagi et al. | |
| 2005/0107708 A1* | 5/2005 | Wrobel | A61B 3/0008 600/476 |
| 2005/0110951 A1* | 5/2005 | Yancey | A61B 3/103 351/221 |
| 2005/0248849 A1 | 11/2005 | Urey | |
| 2006/0045501 A1 | 3/2006 | Liang | |
| 2007/0047059 A1 | 3/2007 | Howard et al. | |
| 2008/0044063 A1* | 2/2008 | Friedman | A61B 3/1216 382/117 |
| 2008/0055698 A1 | 3/2008 | Yurlov | |
| 2008/0144148 A1 | 6/2008 | Kusunose et al. | |
| 2008/0246919 A1 | 10/2008 | Smith | |
| 2008/0269731 A1 | 10/2008 | Swinger et al. | |
| 2009/0059359 A1 | 3/2009 | Nahm et al. | |
| 2010/0157622 A1 | 6/2010 | Stocks | |
| 2011/0144745 A1 | 6/2011 | Martin et al. | |
| 2011/0237999 A1* | 9/2011 | Muller | A61F 9/008 604/20 |
| 2011/0292344 A1* | 12/2011 | Papac | A61B 3/0008 351/221 |
| 2012/0081786 A1 | 4/2012 | Mizuyama | |
| 2012/0203075 A1* | 8/2012 | Horvath | A61B 1/07 600/249 |
| 2012/0215155 A1* | 8/2012 | Muller | A61F 9/0079 604/20 |
| 2012/0257166 A1* | 10/2012 | Francis | G02B 21/0028 351/208 |
| 2013/0144278 A1* | 6/2013 | Papac | A61F 9/00821 606/4 |
| 2013/0150839 A1 | 6/2013 | Smith et al. | |
| 2013/0158392 A1 | 6/2013 | Papac et al. | |
| 2013/0158393 A1 | 6/2013 | Papac et al. | |
| 2013/0338648 A1 | 12/2013 | Hanebuchi et al. | |
| 2014/0333978 A1* | 11/2014 | Hereen | A61B 5/0062 359/210.2 |
| 2014/0350368 A1 | 11/2014 | Irisawa | |
| 2015/0002817 A1* | 1/2015 | Alasaarela | A61B 3/12 351/208 |
| 2015/0042996 A1* | 2/2015 | Funamoto | G01J 3/50 356/402 |
| 2015/0277137 A1 | 10/2015 | Aschwanden | |
| 2015/0366443 A1 | 12/2015 | Liolios et al. | |
| 2018/0012359 A1* | 1/2018 | Prentasic | G06T 7/0014 |
| 2018/0055355 A1* | 3/2018 | Sarunic | A61B 3/1233 |
| 2018/0214018 A1 | 8/2018 | Dos Santos et al. | |
| 2018/0214021 A1 | 8/2018 | Dos Santos et al. | |
| 2018/0214237 A1 | 8/2018 | Dos Santos et al. | |
| 2018/0214238 A1 | 8/2018 | Dos Santos et al. | |
| 2018/0214239 A1 | 8/2018 | Dos Santos et al. | |

FOREIGN PATENT DOCUMENTS

| | | |
|---|---|---|
| EP | 3035110 A1 | 6/2016 |
| GB | 2467181 A | 7/2010 |
| KR | 20110011052 A | 2/2011 |
| WO | 9314432 A2 | 7/1993 |
| WO | WO2012122677 A1 | 9/2012 |
| WO | WO2014053562 A1 | 4/2014 |
| WO | WO2014059552 A1 | 4/2014 |

* cited by examiner

PIXELATED ARRAY OPTICS FOR MIXED MODE SURGICAL LASER ILLUMINATION

BACKGROUND

Field of the Disclosure

The present disclosure relates to surgical illumination, and more specifically, to pixelated array optics for mixed mode surgical laser illumination.

Description of the Related Art

In ophthalmology, eye surgery, or ophthalmic surgery, is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

Additionally, an illumination source is typically introduced into the fundus to illuminate the area where the surgeon will be working. The illumination source is typically implemented as a surgical tool having an illuminator assembly that also penetrates the sclera and may be combined with other surgical tools. The use of optical fibers transmitting coherent light as illumination sources for surgery is desirable because of the high light intensity provided within very small physical dimensions available with optical fibers.

SUMMARY

The disclosed embodiments of the present disclosure provide pixelated array optics for mode mixing to homogenize different modes in an optical fiber used for surgical illumination. A pixelated phase array, such as a digital micromirror device or an LCD phase plate, may impart motion to an incident beam entering the optical fiber to generate a homogeneous illumination field from a coherent light source.

In one aspect, a disclosed method is for surgical illumination. The method may include projecting first light from a coherent light source onto a pixelated phase array to generate second light transmitted from the pixelated phase array, and controlling the pixelated phase array to direct the second light onto a focal spot at a fiber core of an optical fiber, the second light used for illumination of a patient during a surgery. In the method, focal spot is moved over the fiber core. The method may further include transmitting the second light from the optical fiber to a second optical fiber that projects the second light onto the patient.

In any of the disclosed embodiments of the method, the surgery may be an ophthalmic surgery, while the second optical fiber may project the second light into an eye of the patient. The method may further include measuring an intensity of the second light from the optical fiber, and based on the intensity measured, controlling the pixelated phase array to limit movement of the focal spot to the fiber core.

In any of the disclosed embodiments of the method, the coherent light source may be a monochromatic laser.

In any of the disclosed embodiments of the method, the coherent light source may be a plurality of monochromatic lasers combined to generate the first light.

In any of the disclosed embodiments of the method, the pixelated phase array may be a digital micromirror device, while the method operations for controlling the pixelated phase array further include controlling the digital micromirror device that reflects the second light onto the fiber core.

In any of the disclosed embodiments of the method, the pixelated phase array may be a liquid crystal display phase plate, while the method operations for controlling the pixelated phase array further include controlling the liquid crystal display phase plate that transmits the second light onto the fiber core.

In any of the disclosed embodiments, the method operations for projecting the first light onto the pixelated phase array may further include projecting the first light onto the pixelated phase array using a first condenser lens. The method operations for controlling the pixelated phase array to focus the second light onto the focal spot may further include focusing the second light using a second condenser lens.

In any of the disclosed embodiments of the method, the pixelated phase array may impart at least one of a reciprocal motion and a circular motion to the focal spot.

In any of the disclosed embodiments of the method, the pixelated phase array may impart a randomized motion to the focal spot.

In any of the disclosed embodiments of the method, the coherent light source may be a third optical fiber receiving the first light from a laser, while the pixelated phase array may be included in a pixelated phase array device further comprising an input optical connector for connection to the third optical fiber, an output optical connector for connection to the optical fiber, and a power source to power the pixelated phase array.

In another aspect, a device for surgical illumination is disclosed. The device may include a coherent light source for generating first light for illumination of a patient during a surgery, and a pixelated phase array for receiving the first light for generating second light transmitted from the pixeleted phase array, including focusing the second light onto a focal spot at a fiber core of an optical fiber. In the device, the focal spot is moved over the fiber core. The device may further include a second optical fiber receiving the second light, the second optical fiber projecting the second light onto the patient.

In any of the disclosed embodiments of the device, the surgery may be an ophthalmic surgery, while the second optical fiber may project the second light into an eye of the patient. The device may further include an optical intensity sensor to measure an intensity of the second light from the optical fiber, such that the pixelated phase array may be controlled based on the intensity measured to limit movement of the focal spot to the fiber core.

In any of the disclosed embodiments of the device, the coherent light source may be a monochromatic laser.

In any of the disclosed embodiments of the device, the coherent light source may be a plurality of monochromatic lasers combined to generate the first light.

In any of the disclosed embodiments of the device, the pixelated phase array may be a digital micromirror device, while the second light may reflect from the digital micromirror device onto the fiber core.

In any of the disclosed embodiments of the device, the pixelated phase array may be a liquid crystal display phase plate, while the second light may be transmitted from the liquid crystal display phase plate onto the fiber core, and a second condenser lens for focusing the second light onto the focal spot.

In any of the disclosed embodiments, the device may further include a first condenser lens for projecting the first light onto the pixelated phase array.

In any of the disclosed embodiments of the device, the pixelated phase array may impart at least one of a reciprocal motion and a circular motion to the focal spot.

In any of the disclosed embodiments of the device, the pixelated phase array may impart a randomized motion to the focal spot.

In any of the disclosed embodiments of the device, the coherent light source may be a third optical fiber receiving the first light from a laser, while the pixelated phase array may be included in a pixelated phase array device further including an input optical connector for connection to the third optical fiber, an output optical connector for connection between the optical fiber and a fourth optical fiber directly coupled to the second optical fiber, and a power source to power the pixelated phase array.

BRIEF DESCRIPTION OF THE DRAWINGS

For a more complete understanding of the present disclosure and its features and advantages, reference is now made to the following description, taken in conjunction with the accompanying drawings, in which.

DESCRIPTION

Figure 1:
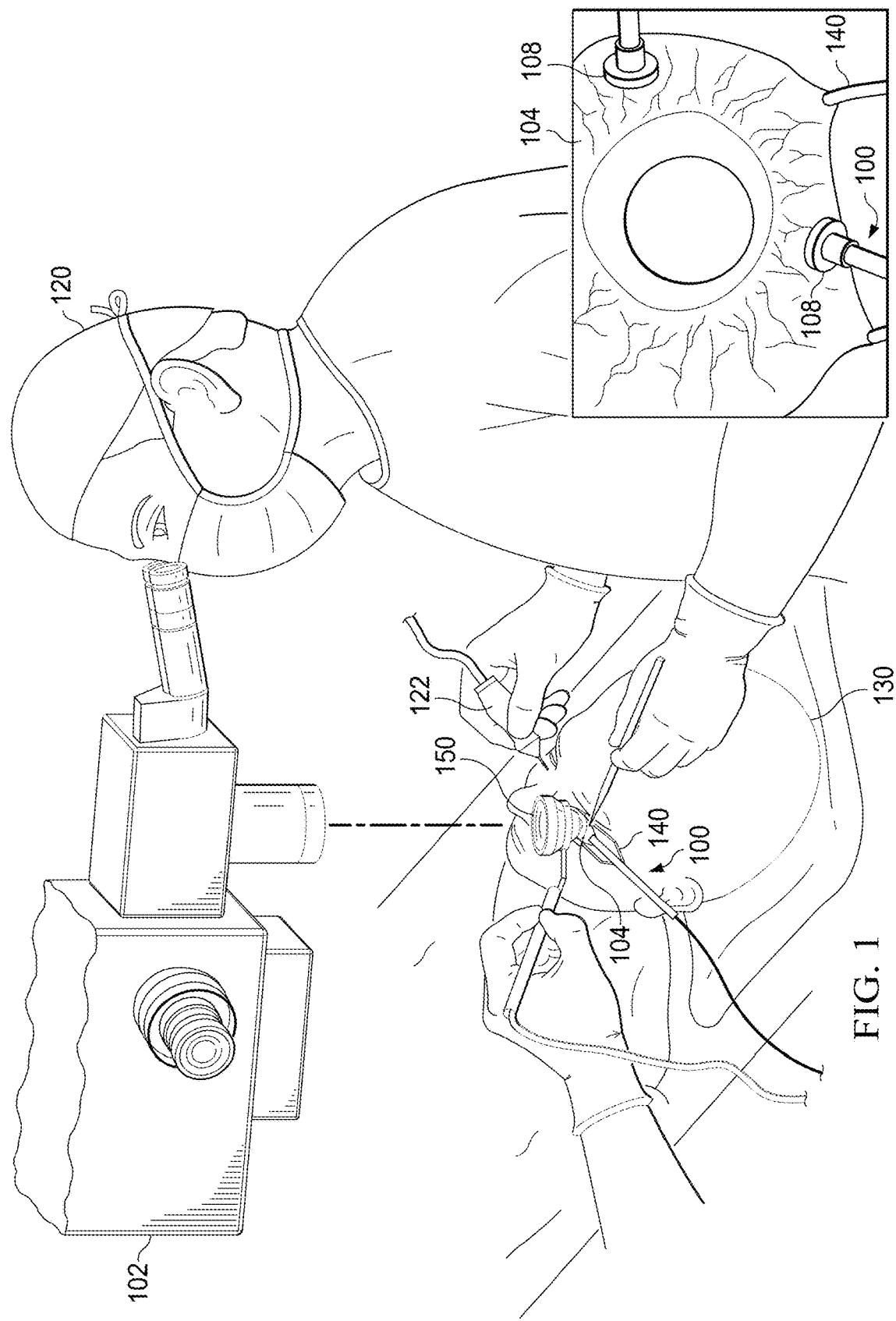
FIG. 1 is a depiction of an embodiment of an ophthalmic surgery using a surgical microscope and a surgical tool with an illuminator assembly.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, the use of optical fibers and coherent light sources is desirable for surgical illumination because of the high light intensity provided within the very small physical dimensions of an optical fiber. Although such surgical illumination sources may be used in various medical and surgical applications, one exemplary application is in eye surgery, such as for vitreoretinal surgery.

For vitreoretinal surgery, for example, the illumination source is typically implemented as a surgical tool having an illuminator assembly that penetrates the sclera and may be combined with other surgical tools. At a distal end of the illuminator assembly, a very small diameter optical fiber may be used to project light into the fundus to illuminate surgical procedures performed within the eye. The very small diameter fiber, for example having a fiber core of about 25-100 µm, is typically coupled to an optical fiber that couples proximally to a coherent light source, such as a laser source. Although various types of optical fibers may be used, multi-mode optical fibers may be used to transmit coherent light into the eye for illumination.

However, as coherent light is transmitted through a multi-mode optical fiber, different groups of photons of the coherent light, referred to as "modes", within the fiber may traverse slightly different path lengths. As a result of the different path lengths experienced by different modes within the optical fiber, the modes may constructively and destructively interfere with each other during propagation within the optical fiber. As the different modes exit the optical fiber from a fiber core, an illumination field provided by the exiting light may appear inhomogeneous due to the inter-mode interference. The inter-mode interference may be highly sensitive to temperature, fiber strain, fiber motion, and may generally become quite noticeable to the human eye, since the inhomogeneous illumination field projects an undesired dynamic pattern, instead of a homogeneous illumination field projecting uniform background light. Because the inhomogeneous illumination field appears as different regions of different colored light that may be dynamic, the inhomogeneous illumination field may be poorly suited for surgical illumination.

For example, in vitreoretinal surgery, a clear and unambiguous view of various fine biostructures in the eye is highly desirable to enable a surgeon to operate safely and effectively, which the inhomogeneous illumination field may not provide. In particular, the inhomogeneous illumination field is observed with monochromatic laser sources, or combinations of monochromatic laser sources in some implementations. The monochromatic laser sources may exhibit fewer modes and, thus, a lesser degree of mode mixing within the optical fiber that enables homogenization of the coherent light into a desired homogeneous illumination field. Furthermore, as various surgical tools are designed and implemented, such as endoilluminators or surgical tools with combined illumination, the use of smaller fiber diameters carrying high light intensity becomes increasingly desirable. However, the inter-mode interference issues become increasingly exacerbated as the size (i.e., diameter) of an optical fiber decreases, which may undesirably constrain the use of such compact illumination systems. Also, in surgical illumination applications, a relatively short length of optical fiber is used, such as about 2-3 m in length. Because mode mixing that leads to a more homogeneous illumination field increases with fiber length, shorter optical fibers used in in surgical illumination applications may experience insufficient mode mixing that results in the inhomogeneous illumination field. Also, optical fibers comprised of a glass core may exhibit fewer modes and less mode mixing, and may be particularly subject to the inhomogeneous illumination field.

As will be described in further detail, pixelated array optics for mixed mode surgical laser illumination are disclosed. The pixelated array optics for mixed mode surgical laser illumination disclosed herein may provide a homogeneous illumination field for surgical illumination using optical fibers to transmit coherent light. The pixelated array optics for mixed mode surgical laser illumination disclosed herein may be used with relatively short and relatively small diameter optical fibers. The pixelated array optics for mixed mode surgical laser illumination disclosed herein may be used with optical fibers having a glass core. The pixelated array optics for mixed mode surgical laser illumination disclosed herein may be implemented at a light source for surgical illumination. The pixelated array optics for mixed mode surgical laser illumination disclosed herein may be implemented as an optical device that can be coupled to an optical fiber providing surgical illumination from a coherent light source. The pixelated array optics for mixed mode surgical laser illumination disclosed herein may be used for illumination of a patient's eye during ophthalmic surgery, such as vitreoretinal surgery.

One manner in which an illumination assembly 100 may be used is illustrated in FIG. 1, in which a surgeon 120 is performing an ophthalmic surgery on an eye 104 of a patient 130 using a surgical tool 122. In FIG. 1, the eye 104 has been exposed using a speculum 140 and a contact lens 150 is held in place on the eye 104 and visually aligned with a surgical microscope 102 to facilitate visualization of inner structures of the eye 104. The surgeon 120 is using the surgical tool 122 to perform surgery on inner structures of the eye 104.

For example, when the surgical tool 122 is a vitrectomy probe, then the surgeon 120 may be using the surgical tool 122 to remove the clear, gel-like vitreous that normally fills the interior of the eye 104, taking care to remove substantially only the vitreous, while avoiding interaction with nearby eye structures, such as the retina, that are extremely sensitive to any mechanical action. The ability of the surgeon to clearly view the fundus is facilitated by a homogenous illumination field that is provided by illumination assembly 100. It is noted that surgical tool 122 may by any of a variety of handheld surgical tools. In some embodiments, illumination assembly 100 may be integrated within surgical tool 122 to provide illumination without having to use a secondary illumination tool.

In the inset of FIG. 1, additional details of the eye 104 during surgery are shown. Two scleral ports 108 for providing cannulated scleral penetration are visible, one for surgical tool 122 and one for illuminator assembly 100. As shown, illuminator assembly 100 may include pixelated array optics for mixed mode surgical laser illumination, as described in further detail below. Accordingly, illuminator assembly 100 may be used to project coherent light into the eye 104 using an optical fiber to transmit the light to project a homogenous illumination field (not visible in FIG. 1) into the fundus.

Modifications, additions, or omissions may be made to illuminator assembly 100 without departing from the scope of the disclosure. The components and elements of surgical illuminator assembly 100, as described herein, may be integrated or separated according to particular applications. Illuminator assembly 100 may be implemented using more, fewer, or different components in some embodiments.

Figure 2:
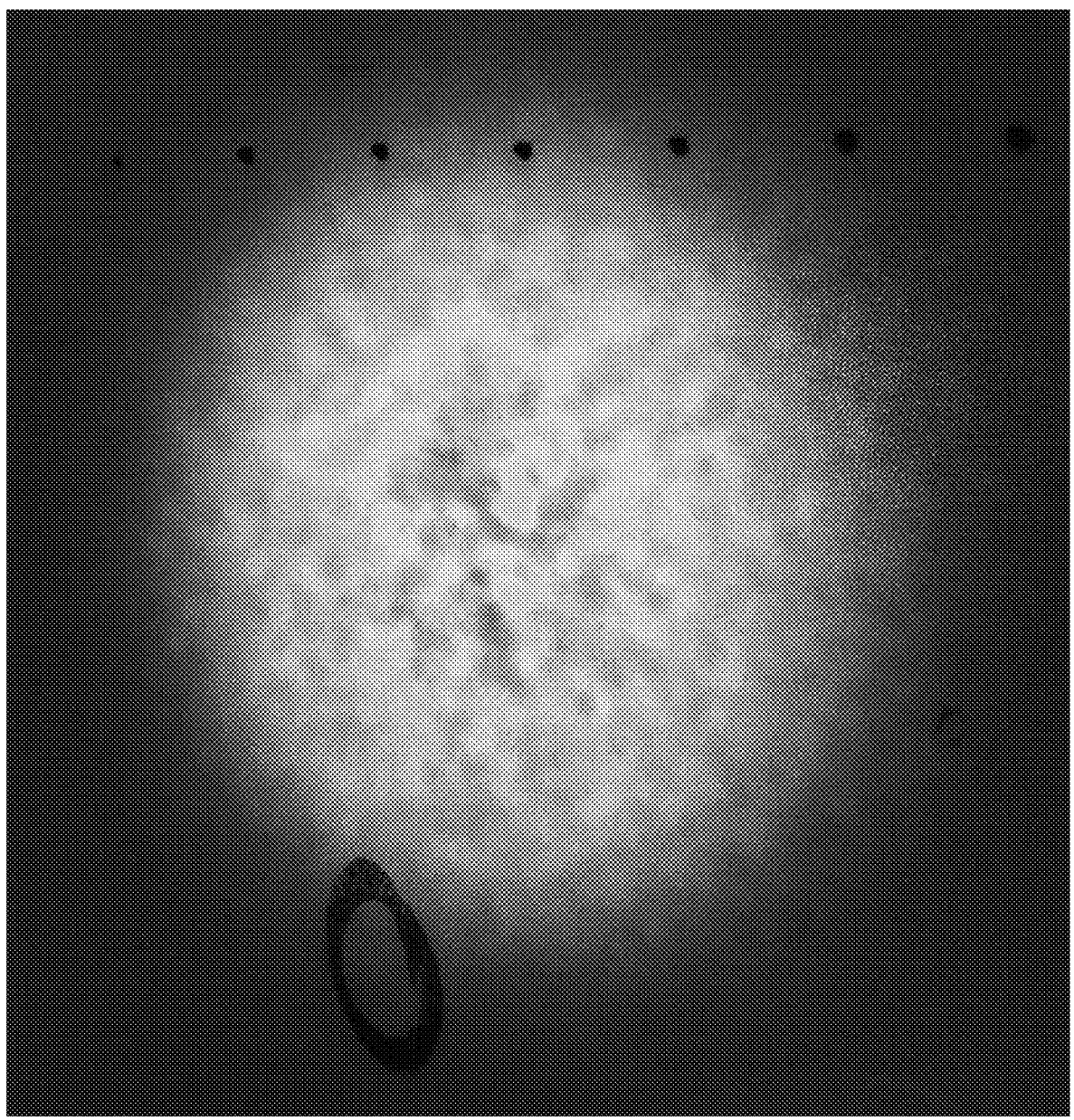
FIG. 2 is an image of inhomogeneous light from fiber modes.

FIG. 2 illustrates an image 200 of inhomogeneous light from fiber modes. Image 200 depicts coherent light from an optical fiber projected onto a screen that is oriented oblique to the page. In image 200, the depicted screen has extraneous annotations written in black ink above and below an inhomogeneous illumination field. The inhomogeneous illumination field in image 200 results from insufficient mode mixing within the optical fiber. The inhomogeneous illumination field in image 200 may exhibit intensity variations up to about 500%, which may be dynamic in many applications and usage scenarios, which is undesirable for surgical illumination, as explained previously. The inhomogeneous illumination field in image 200 may be immediately converted into a homogeneous illumination field, such as a substantially uniform intensity illumination field (not shown) by applying the techniques for mode mixing disclosed herein.

Figure 3:
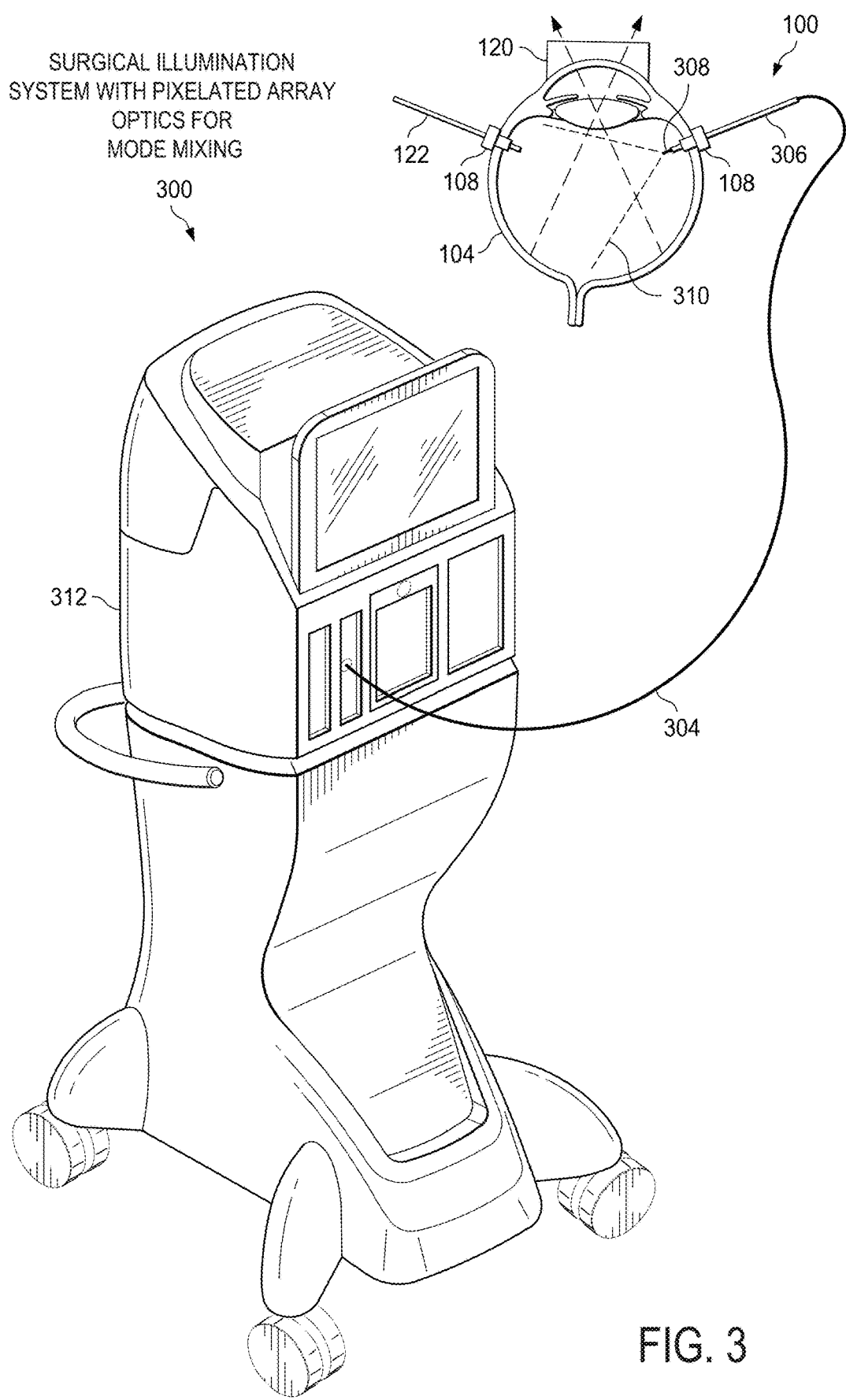
FIG. 3 is a depiction of an embodiment of a surgical illumination system with pixelated array optics for mode mixing.

Referring now to FIG. 3, a depiction of an embodiment of a surgical illumination system 300 is shown. As shown in FIG. 3, surgical illumination system 300 may be used in the ophthalmic surgery on the eye 104 shown in FIG. 1. FIG. 3 is a schematic illustration and is not drawn to scale or perspective. In FIG. 3, a cross-sectional view of the eye 104 is shown, enabling a view of various elements described above with respect to FIG. 1. Specifically, contact lens 120 is shown providing a relatively wide angle view of the fundus of the eye 104, while two scleral ports 108 penetrate the sclera of the eye 104. A surgical tool 122 is shown penetrating one scleral port 108, while illumination assembly penetrates another scleral port 108.

As shown in FIG. 3, a homogeneous illumination field 310 is projected into the eye 104 by illuminator assembly 100. Specifically, illuminator assembly 100 terminates distally with an optical fiber portion 308, which may be exposed to project light into the eye. Optical fiber portion 308 is coupled to an external optical fiber 304. In some embodiments, optical fiber portion 308 may be a distal portion of external optical fiber 304 itself. Optical fiber 304 is shown passing through a hand piece 306, which may include a sheath or tube around optical fiber 304 to enable cannulation at scleral port 108. Optical fiber 304 is shown extending from a surgical console 312 to hand piece 306.

In FIG. 3, surgical console 312 may include pixelated array optics for mixed mode surgical laser illumination, as disclosed herein. In some embodiments, the pixelated array optics for mixed mode surgical laser illumination may be implemented as a separate device (see FIGS. 4D and 4E). Specifically, surgical console 312 may include a light source comprised of a laser source and a condenser lens (or equivalent optical element). The condenser lens may focus first light generated by the laser source onto a focal spot at a pixelated phase array that is electronically controlled. The pixelated phase array may apply a phase shift to individual pixel elements to direct and focus the received light towards a fiber core of optical fiber 304 at a proximal end. The pixelated phase array may be a digital micromirror device or an LCD phase plate. In this manner, the focal spot is moved over the fiber core to generate second light that is transmitted by optical fiber 304. Because movement of the focal spot creates or enhances mode mixing in optical fiber 304, the second light may provide a homogeneous illumination field 310 in the eye 104 after exiting optical fiber portion 308, which is at a distal end of optical fiber 304.

Surgical console 312 may provide various other equipment and functionality, such as driver equipment for surgical tool 122, and a user interface for data operations and image processing. Further internal details of the pixelated array optics for mixed mode surgical laser illumination are described below with respect to FIGS. 4A, 4B, 4C, 4D, and 4E.

Figure 4A:
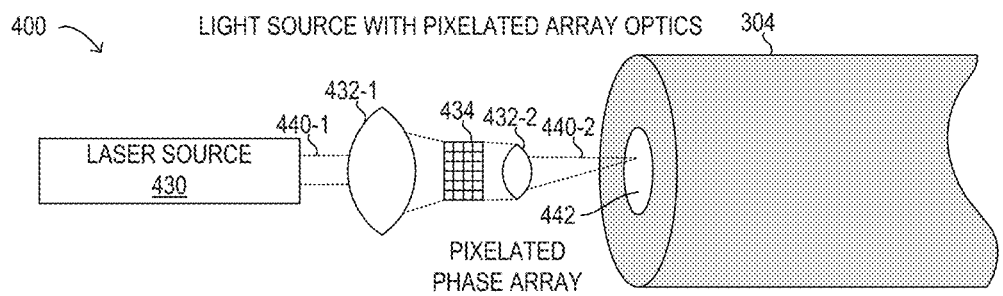
FIG. 4A is a depiction of an embodiment of a light source with pixelated array optics.

Referring now to FIG. 4A, a depiction of an embodiment of a light source 400 with pixelated array optics is shown. FIG. 4A is a schematic illustration and is not drawn to scale or perspective. In FIG. 4A, elements included within light source 400 are shown schematically from a side view. It will be understood that light source 400 may be implemented as an optical device, for example having an enclosure (not shown) to house the components illustrated in FIG. 4A. In particular embodiments, light source 400 may be included with or integrated with surgical console 312 (see FIG. 3), where optical fiber 304 may begin at a proximal end.

In light source 400, a laser source 430 may represent a source of coherent light. Laser source 430 may represent a monochromatic light source. Laser source 430 may represent a combination of a plurality of monochromatic light sources, in some embodiments. Laser source 430 may generate first light 440-1, which is coherent light. First light 440-1 may be projected onto a first condenser lens 432-1, which may be used to focus first light 440-1 onto a pixelated phase array 434, which may generate second light 440-2. Then, pixelated phase array 434 may direct second light 440-2 towards a second condenser lens 432-2, which may focus second light 440-2 onto fiber core 442 of optical fiber 304. First light 440-1 may be generated as a collimated laser beam of about 1-5 mm in diameter having an optical power in the range of about 10-500 mW in various embodiments. First light 440-1 may be focused onto a focal spot that is about 5-10 μm in diameter by pixelated phase array 434 using second condenser lens 432-2. The focal spot may be less than 20 μm in diameter, or less than 25 μm in diameter in various embodiments. Fiber core 442 may be as small as about 30 μm in diameter. In some embodiments, fiber core 442 may about 50 μm in diameter, or about 100 μm in diameter, or various diameter sizes therebetween.

As shown in FIG. 4A, pixelated phase array 434 may impart at least one of a reciprocal motion and a circular motion to second light 440-2. In some embodiments, pixelated phase array 434 may impart a randomized motion to second light 440-2. In different embodiments, pixelated phase array 434 may cause second light 440-2 to reciprocate, rotate, or oscillate at a frequency to cause motion that is not visible to the human eye, such as at a frequency of about 30 Hz or greater.

Figure 4B:
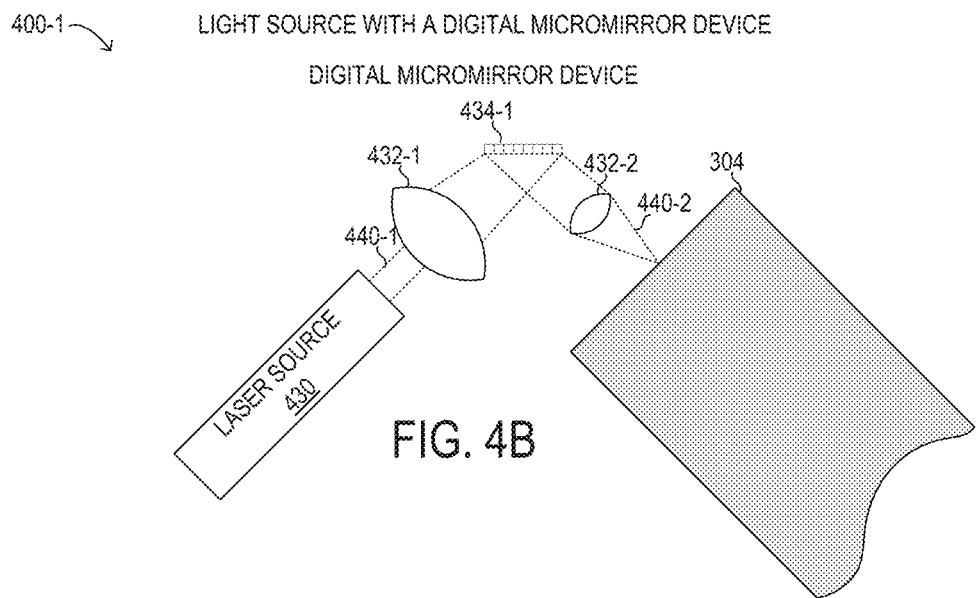
FIG. 4B is a depiction of an embodiment of a light source with a digital micromirror device.

Referring now to FIG. 4B, a depiction of an embodiment of a light source 400-1 with pixelated array optics comprising a digital micromirror device 434-1 is shown. FIG. 4B is a schematic illustration that includes similar elements as FIG. 4A and is not drawn to scale or perspective. In FIG. 4B, elements included within light source 400-1 are shown schematically from a top view. The arrangement of digital micromirror device 434-1 enables digital micromirror device 434-1 to operate in reflection. It will be understood that light source 400-1 may be implemented as an optical device, for example having an enclosure (not shown) to house the components illustrated in FIG. 4B. In particular embodiments, light source 400-1 may be included with or integrated with surgical console 312 (see FIG. 3), where optical fiber 304 may begin at a proximal end.

Figure 4C:
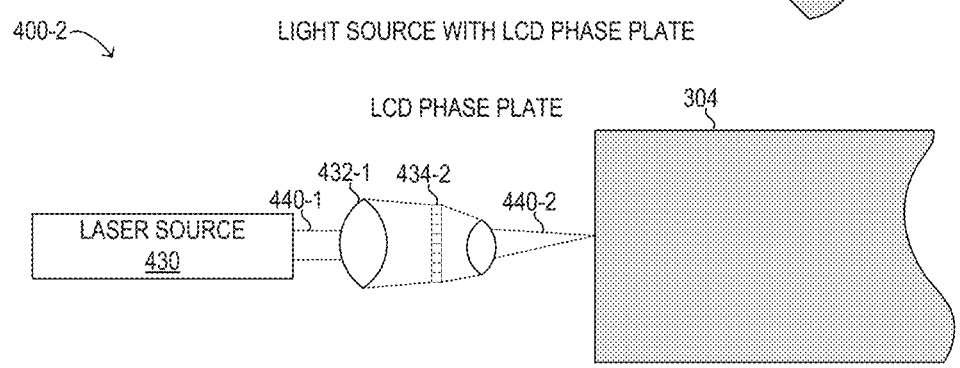
FIG. 4C is a depiction of an embodiment of a light source with an LCD phase plate.

Referring now to FIG. 4C, a depiction of an embodiment of a light source 400-2 with pixelated array optics comprising an LCD phase plate 434-2 is shown. FIG. 4C is a schematic illustration that includes similar elements as FIG. 4A and is not drawn to scale or perspective. In FIG. 4C, elements included within light source 400-2 are shown schematically from a top view. The arrangement of LCD phase plate 434-2 enables LCD phase plate 434-2 to operate in transmission. It will be understood that light source 400-2 may be implemented as an optical device, for example having an enclosure (not shown) to house the components illustrated in FIG. 4C. In particular embodiments, light source 400-2 may be included with or integrated with surgical console 312 (see FIG. 3), where optical fiber 304 may begin at a proximal end.

Figure 4D:
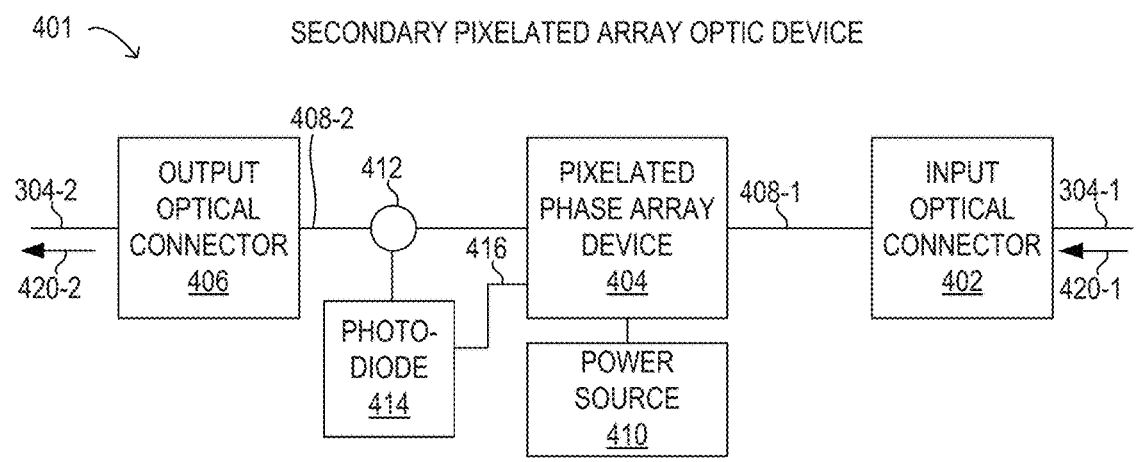
FIG. 4D is a depiction of an embodiment of a secondary pixelated array optic device.

Referring now to FIG. 4D, a depiction of an embodiment of a secondary pixelated array optic device 401 is shown. FIG. 4D is a schematic illustration and is not drawn to scale or perspective. In FIG. 4D, elements included within secondary pixelated array optic device 401 are shown schematically. It will be understood that secondary pixelated array optic device 401 may be implemented as an optical device, for example having an enclosure (not shown) to house the components illustrated in FIG. 4D. In particular embodiments, secondary pixelated array optic device 401 may be installed along optical fiber 304 as an intermediate optical device, while optical fiber 304 may be implemented in two sections with the appropriate optical connectors.

Specifically, secondary pixelated array optic device 401 is shown having input optical connector 402 for connecting to optical fiber 304-1, as well as having output optical connector 406 for connecting to optical fiber 304-2. In various embodiments, input optical connector 402 and output optical connector 406 may be releasable connectors (not shown) that mate with corresponding connectors attached to optical fibers 304-1 and 304-2. In some embodiments, input optical connector 402 and output optical connector 406 may be fixed connectors. As shown, input optical connector 402 couples to a first internal optical fiber 408-1 that connects to a pixelated phase array device 404. Pixelated phase array device 404 may connect to output optical connector 406 using a second internal optical fiber 408-2.

In secondary pixelated array optic device 401, input optical connector 402 may receive first light 420-1, which may experience insufficient mode mixing in optical fiber 304-1 after being transmitted from a coherent light source. The coherent light source may be a monochromatic laser, or a combination of monochromatic lasers that have been combined to generate first light 420-1. Accordingly, first light 420-1 may include light from different frequencies (i.e., colors). First light 420-1 is transmitted by first internal optical fiber 408-1 to pixelated phase array device 404, which is similar to light source 400, and is described in further detail below with respect to FIG. 4E. Pixelated phase array device 404 may output second light 420-2 that has been mode mixed to second internal optical fiber 408-2, which connects to output optical connector 406.

As shown in FIG. 4D, an optical tap 412 may be used along second internal optical fiber 408-2 to divert some optical energy from second light 420-2 to a photodiode 414 (or another optical intensity sensor). A feedback control signal 416 from photodiode 414 may be used by pixelated phase array device 404 to regulate the operation of pixelated phase array 434 (included within pixelated phase array device 404), such that an output beam (second light 440-2) of pixelated phase array 434 remains directed at fiber core 442. When the output beam of pixelated phase array 434 is not directed at fiber core 442, the intensity measured by photodiode 414 will decrease (assuming constant optical power at the coherent light source). In this manner, feedback control signal 416 may enable regulation of the operation of pixelated phase array 434 in a desired manner.

Also shown with secondary pixelated array optic device 401 in FIG. 4D is power source 410, which may provide power to pixelated phase array 434 included with pixelated phase array device 404. In some embodiments, power source 410 may represent an internal power source to secondary pixelated array optic device 401, such as a battery to enable remote operation. In other embodiments, power source 410 may represent an external power source, such as a connector for line power or direct current from an external power supply (not shown).

Figure 4E:
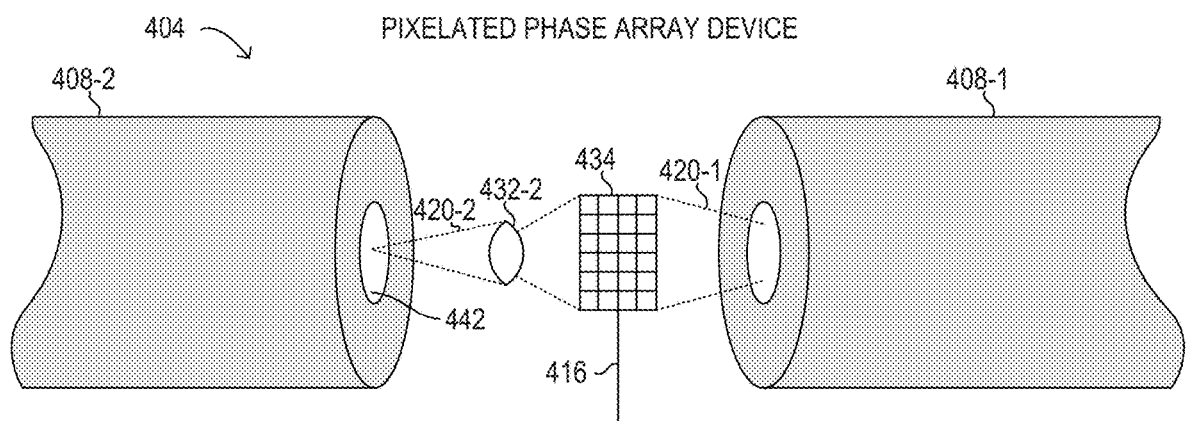
FIG. 4E is a depiction of an embodiment of a pixelated phase array device.

Referring now to FIG. 4E, a depiction of an embodiment of pixelated phase array device 404 (see also FIG. 4D) is shown. FIG. 4E is a schematic illustration and is not drawn to scale or perspective. In FIG. 4E, elements included within pixelated phase array device 404 are shown schematically. It will be understood that pixelated phase array device 404 may be implemented as an optical device, for example having an enclosure (not shown) to house the components illustrated in FIG. 4E. In particular embodiments, pixelated phase array device 404 may be included with secondary pixelated array optic device 401 described above.

In pixelated phase array device 404, first light 420-1 arrives from first internal optical fiber 408-1, as described previously. For example, first light 420-1 may be collimated by a first condenser lens and transmitted through optical fiber 408-1 at a light source (not visible in FIG. 4E). First light 420-1 may be projected onto pixelated phase array 434, which may be used to redirect first light 440-1 onto a fiber core 442 of second internal optical fiber 408-2 to generate second light 420-2. As shown, second condenser lens 432-2 may be used to focus second light 420-2 onto fiber core 442 from pixelated phase array 434. Pixelated phase array 434 may operate to impart vibration, motion, rotation, or translation to first light 440-1, as described previously. Pixelated phase array 434 is shown receiving feedback control signal 416 as an input for regulation of the redirection of first light 440-1, as described previously.

Figure 5:
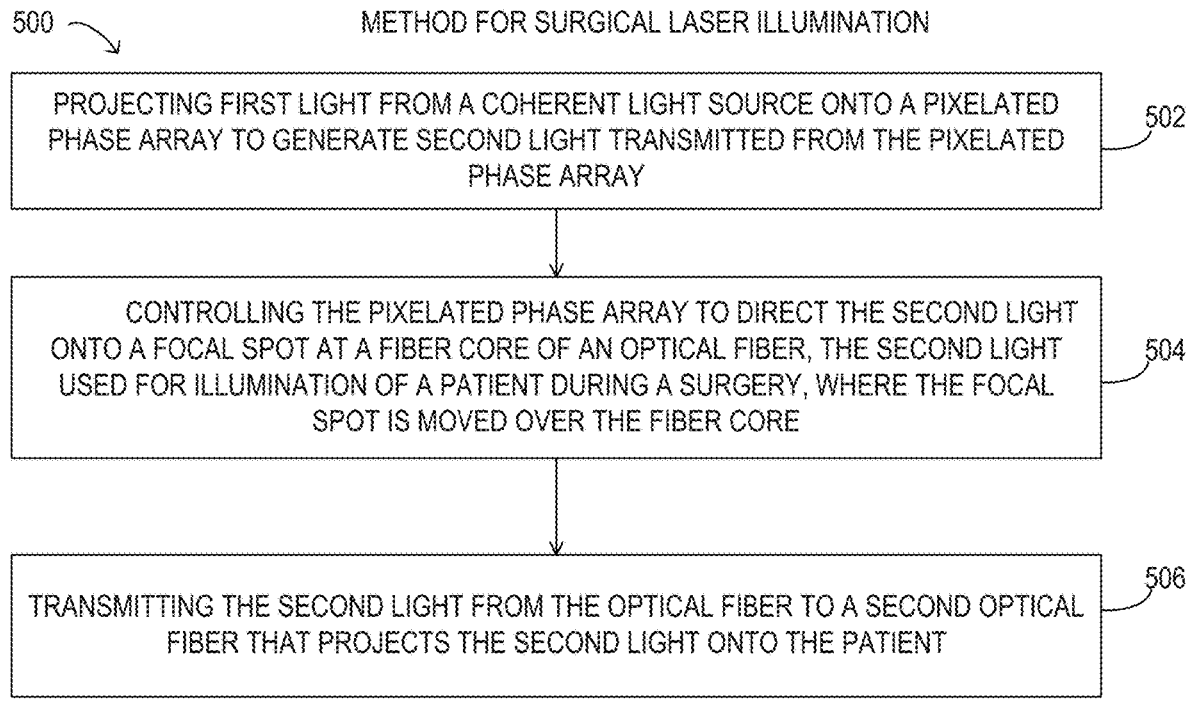
FIG. 5 is a flow chart of selected elements of a method for surgical laser illumination.

Referring now to FIG. 5, a flow chart of selected elements of an embodiment of a method 500 for surgical laser illumination using pixelated array optics for mode mixing, as described herein, is depicted in flowchart form. It is noted that certain operations described in method 500 may be optional or may be rearranged in different embodiments. Method 500 may be performed using illumination assembly 100, along with pixelated array optic light source 400 or secondary pixelated array optic device 402, as described herein.

Method 500 may begin, at step 502, by projecting first light from a coherent light source into a pixelated phase array to generate second light transmitted from the pixelated phase array. At step 504, the pixelated phase array is controlled to direct the second light onto a focal spot at a fiber core of an optical fiber, the second light used for illumination of a patient during a surgery, where the focal spot is moved over the fiber core. At step 506, the second light is transmitted from the optical fiber to a second optical fiber that projects the second light onto the patient.

As disclosed herein, pixelated array optics for mode mixing may be used to homogenize different modes in an optical fiber used for surgical illumination. A pixelated phase array, such as a digital micromirror device or an LCD phase plate, may impart motion to an incident beam entering the optical fiber to generate a homogeneous illumination field from a coherent light source.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for surgical illumination, the method comprising:
projecting first light from a coherent light source onto a pixelated phase array to generate second light transmitted from the pixelated phase array;
controlling the pixelated phase array to direct the second light onto a focal spot at a single fiber core of an optical fiber, wherein the focal spot has a smaller diameter than a diameter of the fiber core, the second light used for illumination of a patient during a surgery, wherein the focal spot is continuously moved over the single fiber core and within the diameter of the fiber core to create mode mixing of the second light in the optical fiber; and
transmitting the second light from the optical fiber to a second optical fiber that projects the second light onto the patient, wherein the created mode mixing causes the second light to provide a homogeneous illumination field onto the patient.

2. The method of claim 1, wherein the surgery is an ophthalmic surgery, and the second optical fiber projects the second light into an eye of the patient, and further comprising:
measuring an intensity of the second light from the optical fiber;
based on the intensity measured, controlling the pixelated phase array to limit movement of the focal spot to the fiber core.

3. The method of claim 1, wherein the coherent light source is a monochromatic laser.

4. The method of claim 1, wherein the coherent light source is a plurality of monochromatic lasers combined to generate the first light.

5. The method of claim 1, wherein the pixelated phase array is a digital micromirror device, and wherein controlling the pixelated phase array further comprises:
controlling the digital micromirror device that reflects the second light onto the fiber core.

6. The method of claim 1, wherein the pixelated phase array is a liquid crystal display phase plate, and wherein controlling the pixelated phase array further comprises:
controlling the liquid crystal display phase plate that transmits the second light onto the fiber core.

7. The method of claim 1, wherein projecting the first light onto the pixelated phase array further comprises:
projecting the first light onto the pixelated phase array using a first condenser lens; and
wherein controlling the pixelated phase array to focus the second light onto the focal spot further comprises:
focusing the second light using a second condenser lens.

8. The method of claim 1, wherein the pixelated phase array imparts at least one of a reciprocal motion and a circular motion to the focal spot.

9. The method of claim 1, wherein the pixelated phase array imparts a randomized motion to the focal spot.

10. The method of claim 1, wherein the coherent light source is a third optical fiber receiving the first light from a laser, and wherein the pixelated phase array is included in a pixelated phase array device further comprising:
- an input optical connector for connection to the third optical fiber;
- an output optical connector for connection to the optical fiber; and
- a power source to power the pixelated phase array.

11. A device for surgical illumination, the device comprising:
- a coherent light source for generating first light for illumination of a patient during a surgery;
- a pixelated phase array for receiving the first light and for generating second light transmitted from the pixelated phase array, including focusing the second light onto a focal spot at a fiber core of a single optical fiber, wherein the focal spot has a smaller diameter than a diameter of the fiber core, wherein the focal spot is continuously moved over the single fiber core and within the diameter of the fiber core to create mode mixing of the second light in the optical fiber; and
- a second optical fiber receiving the second light, the second optical fiber projecting the second light onto the patient, wherein the created mode mixing causes the second light to provide a homogeneous illumination field onto the patient.

12. The device of claim 11, wherein the surgery is an ophthalmic surgery, and the second optical fiber projects the second light into an eye of the patient, and further comprising:
- an optical intensity sensor to measure an intensity of the second light from the optical fiber, wherein the pixelated phase array is controlled based on the intensity measured to limit movement of the focal spot to the fiber core.

13. The device of claim 11, wherein the coherent light source is a monochromatic laser.

14. The device of claim 11, wherein the coherent light source is a plurality of monochromatic lasers combined to generate the first light.

15. The device of claim 11, wherein the pixelated phase array is a digital micromirror device, and wherein the second light reflects from the digital micromirror device onto the fiber core.

16. The device of claim 11, wherein the pixelated phase array is a liquid crystal display phase plate, and wherein the second light is transmitted from the liquid crystal display phase plate onto the fiber core.

17. The device of claim 11, further comprising:
- a first condenser lens for projecting the first light onto the pixelated phase array; and
- a second condenser lens for focusing the second light onto the focal spot.

18. The device of claim 11, wherein the pixelated phase array imparts at least one of a reciprocal motion and a circular motion to the focal spot.

19. The device of claim 11, wherein the pixelated phase array imparts a randomized motion to the focal spot.

20. The device of claim 11, wherein the coherent light source is a third optical fiber receiving the first light from a laser, and wherein the pixelated phase array is included in a pixelated phase array device further comprising:
- an input optical connector for connection to the third optical fiber;
- an output optical connector for connection between the optical fiber and a fourth optical fiber directly coupled to the second optical fiber; and
- a power source to power the pixelated phase array.

* * * * *